(12) United States Patent
Paul

(10) Patent No.: US 6,475,240 B1
(45) Date of Patent: Nov. 5, 2002

(54) ANTERIOR CHAMBER INTRAOCULAR LENS AND METHODS FOR REDUCING PUPIL OVALLING

(75) Inventor: Marlene L. Paul, Laguna Niguel, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 0 days.

(21) Appl. No.: 09/496,519

(22) Filed: Feb. 2, 2000

(51) Int. Cl.⁷ .................................................. A61F 2/16
(52) U.S. Cl. ...................... 623/6.52; 623/6.49; 623/6.53
(58) Field of Search ................................ 623/FOR 105, 623/6.11, 6.37–6.55, 6.18, 6.36

(56) References Cited

U.S. PATENT DOCUMENTS

| | | | |
|---|---|---|---|
| 4,077,071 A | * | 3/1978 | Freeman ..................... 623/6.43 |
| 4,174,543 A | | 11/1979 | Kelman |
| 4,249,272 A | | 2/1981 | Poler |
| 4,254,509 A | | 3/1981 | Tennant |
| 4,254,510 A | | 3/1981 | Tennant |
| 4,316,293 A | | 2/1982 | Bayers |
| 4,370,760 A | | 2/1983 | Kelman |
| 4,377,873 A | | 3/1983 | Reichert, Jr. |
| 4,403,353 A | | 9/1983 | Tennant |
| 4,404,694 A | | 9/1983 | Kelman |
| 4,424,597 A | | 1/1984 | Schlegel |
| 4,446,581 A | | 5/1984 | Blake |
| 4,480,340 A | * | 11/1984 | Shepard ..................... 623/6.51 |
| 4,551,864 A | | 11/1985 | Akhavi |
| 4,556,998 A | | 12/1985 | Siepser |
| 4,560,383 A | | 12/1985 | Leiske |
| 4,605,409 A | | 8/1986 | Kelman |
| 4,605,411 A | | 8/1986 | Fedorov et al. |
| 4,629,460 A | | 12/1986 | Dyer |
| 4,629,462 A | | 12/1986 | Feaster |
| 4,676,791 A | | 6/1987 | LeMaster et al. |
| 4,676,792 A | | 6/1987 | Praeger |
| 4,687,484 A | | 8/1987 | Kaplan |
| 4,687,485 A | | 8/1987 | Lim et al. |
| 4,725,277 A | | 2/1988 | Bissonette |
| 4,734,095 A | | 3/1988 | Siepser |
| 4,781,717 A | | 11/1988 | Grendahl |
| 4,787,904 A | | 11/1988 | Severin |
| RE32,525 E | | 5/1989 | Pannu |
| 5,047,052 A | | 9/1991 | Dubroff |
| 5,071,432 A | | 12/1991 | Baikoff |
| 5,078,742 A | | 1/1992 | Dahan |
| 5,133,749 A | | 7/1992 | Nordan |
| 5,147,395 A | | 9/1992 | Willis |
| 5,147,397 A | | 9/1992 | Christ et al. |
| 5,197,981 A | | 3/1993 | Southard |
| 5,203,790 A | | 4/1993 | McDonald |
| 5,225,858 A | | 7/1993 | Portney |
| 5,258,025 A | | 11/1993 | Fedorov et al. |
| 5,628,796 A | | 5/1997 | Suzuki |
| 5,716,403 A | | 2/1998 | Tran et al. |
| 6,015,435 A | | 1/2000 | Valunin et al. |
| 6,051,024 A | * | 4/2000 | Cumming ................... 623/6.44 |

FOREIGN PATENT DOCUMENTS

FR    2745711 A   *   9/1997   ........ 623/FOR 105

OTHER PUBLICATIONS

CILCO advertisement brochure, Oct. 1982, 3 pages.*
Praeger, Copeland Lens, 1982, 7 pages.*

* cited by examiner

Primary Examiner—David H. Willse
(74) Attorney, Agent, or Firm—Stout, Uxa, Buyan & Mullins, LLP; Frank J. Uxa; Peter Jay Gluck

(57) ABSTRACT

An intraocular lens having an optic and a plurality of fixation members coupled to the optic. The fixation members are adapted to be evenly circumferentially distributed about the anterior chamber to reduce the phenomenon of malshaping the iris, for example, pupil ovalling.

22 Claims, 2 Drawing Sheets

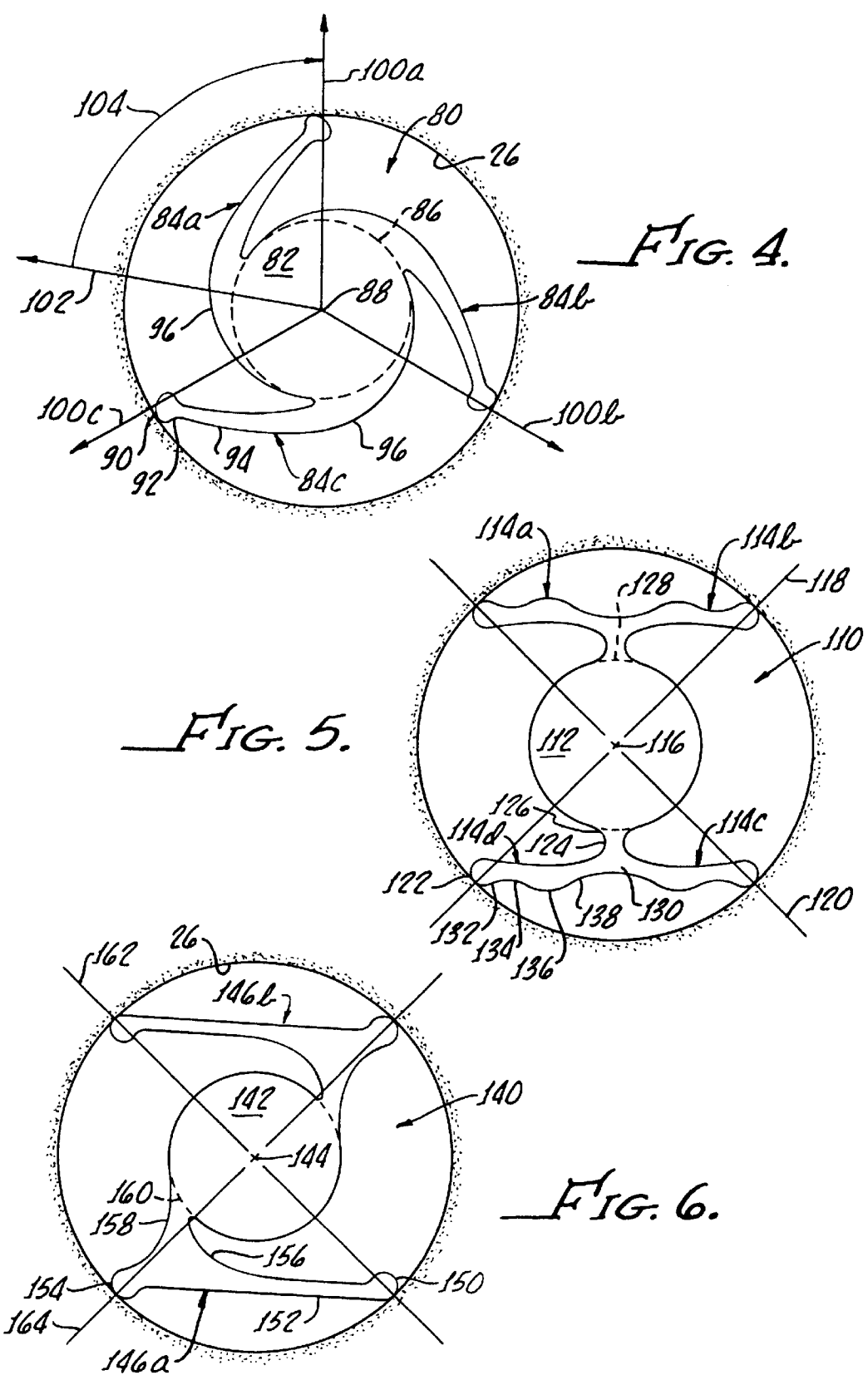

ANTERIOR CHAMBER INTRAOCULAR LENS AND METHODS FOR REDUCING PUPIL OVALLING

BACKGROUND OF THE INVENTION

This invention relates to intraocular lenses (IOLs). More particularly, the invention relates to IOLs placed in the anterior chambers of eyes, and to methods for inserting IOLs in such anterior chambers, which reduce the risk of malshaping the iris of the eye, for example, ovalling the pupil formed by the iris.

Intraocular lenses (IOLs) are commonly used to modify or enhance vision. IOLs can be placed at various positions or locations within the eye. For example, IOLs can be placed in the anterior chamber of the eye, that is, the region of the eye posterior of the cornea and anterior of the iris.

Referring now to FIG. 1, an anterior IOL (AIOL) 10 of the prior art is shown implanted in an eye 12. The eye 12 comprises a cornea 14 shown to the left and an iris 16 shown in the middle of the eye. It is to be understood that the cornea 14 is at the front of the eye 12. The iris 16 divides the eye 12 into an anterior chamber 18 at the front of the eye and a posterior chamber 20 in back of the iris. The iris 16 also defines the pupil 22, which is an opening in the middle of the iris. In front of the iris 16 is the scleral spur 24. The scleral spur 24 and the iris 18 delimit the ciliary band 26. Behind the iris 16 is the ciliary process 28, from which extends the ciliary muscle 30. The ciliary muscle supports the natural crystalline lens 32 of the eye 12. The iris 16 and the ciliary process 28 define the sulcus 34.

FIG. 1 shows the AIOL 10 implanted in the anterior chamber 18 of the eye 12. The AIOL 10 is comprised of an optic 40 that is supported in front of the pupil 22 by fixation members 42, sometimes known as loops or haptics. The optic 40, for the AIOL 10 and other IOL's described herein, may be considered as including an optical portion for focusing light at or near the retina (not shown) of the eye 12. The fixation members 42 extend from the optic 40 to rest in the ciliary band 26, and are designed to minimize compression stress on the optic 40 and inhibit forward vaulting of the optic. If the optic 40 vaults and contacts the cornea 14, an undesirable condition known as endothelium tough may occur. However, this condition may occur from the fixation members 42 merely residing in the ciliary band 26.

Current anterior chamber IOLs have fixation systems that are shorter in one dimension to facilitate passage through a minimum incision size. For example, one AIOL of the prior art includes a rectangular arrangement of footplate haptics. Such AIOLs have a tendency to malshape, e.g., oval, the iris of the eye, which is not acceptable from a cosmetic point of view. In addition, malshaping is an indication of a possible misfit of the IOL, which can result in impaired vision and/or additional surgery to replace the IOL.

It would be advantageous to provide anterior chamber IOLs which reduce the risk of malshaping the iris of the eye.

SUMMARY OF THE INVENTION

New IOLs for implantation in eyes, in particular in anterior chambers of the eyes, have been discovered. The present IOLs effectively reduce the risk of malshaping the iris of the eye, are adapted to be effectively fixated in the anterior chamber of the eye, and provide desired vision correction. In general, the present IOLs include fixation systems which facilitate effectively fixating the IOLs in the anterior chamber of the eye and, in addition, reduce or even substantially eliminate the risk of malshaping the iris. The present IOLs are straightforward in construction and can be produced using conventional and well known techniques. Thus, the present IOLs provide substantial benefits without dramatic changes in IOL design and insertion procedures.

In one broad aspect of the present invention, IOLs for implantation in an eye, in particular an anterior chamber of the eye, are provided. Such IOLs comprise optics and fixation systems. The optic has an optical axis and is effective to direct light toward the retina of the eye. The present IOLs can be employed with or without the natural lens being present. One advantage of having the present IOLs in the anterior chamber of the eye is that the optic of the present IOL is spaced apart from the natural lens, if present. Such separation advantageously protects the natural lens from cataract formation or other detrimental conditions which may be caused by contact between the optic and the natural lens.

The present fixation system is coupled to the optic and includes at least three distal ends extending radially outwardly of the optic. These distal ends are adapted to be in contact with a peripheral region of the anterior chamber of the eye, for example, to facilitate fixating the IOL in the anterior chamber. Each of the distal ends of the fixation system is substantially equidistantly spaced apart from the closest circumferentially adjacent distal ends. This structure is very effective in spreading or equalizing the stress on the peripheral region of the anterior chamber and the iris caused by the presence of the IOL. Such substantial stress uniformity is believed to be one important factor in reducing the risk of malshaping the iris as a result of the presence of the IOL in the anterior chamber. In one embodiment, the IOL of the present invention is made of a material that is resilient enough to be folded for insertion through narrow access passages or incisions into the anterior chamber of the eye.

In addition, the distal ends preferably include a structure enlarged relative to a portion of the fixation system proximal of the distal ends. Such enlarged structure at the distal end is advantageous, for example, in guarding against the harmful effects of excessive contact stresses between the fixation system and the tissue at the peripheral region of the anterior chamber, which is susceptible to being damaged. The present IOLs are effectively fixated in the anterior chamber of the eye and effectively reduce one or more of the detrimental effects often caused by having anterior chamber IOLs fixated in the anterior chamber.

The present IOLs can be produced in any suitable manner. A number of conventional IOL manufacturing techniques, which are well known in the art, are effective. Such techniques include, but are not limited to, polymerization techniques, and/or polymeric material molding, casting and/or machining. The fixation members can be provided, together with the optic, as part of a single piece lens, or can be coupled to the optic during formation of the optic, for example, during polymerization to produce the optic, or after the optic is formed. The specific methodology or methodologies by which the present IOLs are produced is not a critical aspect of the present invention.

Any and all features described herein and combinations of such features are included within the scope of the present invention provided that the features of any such combination are not mutually inconsistent.

These and other aspects and advantages of the present invention will become apparent in the following detailed description and claims, particularly when considered in

BRIEF DESCRIPTION OF THE DRAWINGS

FIG. 4 is a front elevational view of a second embodiment of an intraocular lens of the present invention having three spirally directed fixation members;

FIG. 5 is a front elevational view of a third embodiment of an intraocular lens of the present invention having two pairs of connected fixation members;

FIG. 6 is a front elevational view of a fourth embodiment of an intraocular lens of the present invention also having two fixation members, each defining two points of contact with the eye.

DESCRIPTION OF THE PREFERRED EMBODIMENTS

Figure 1:
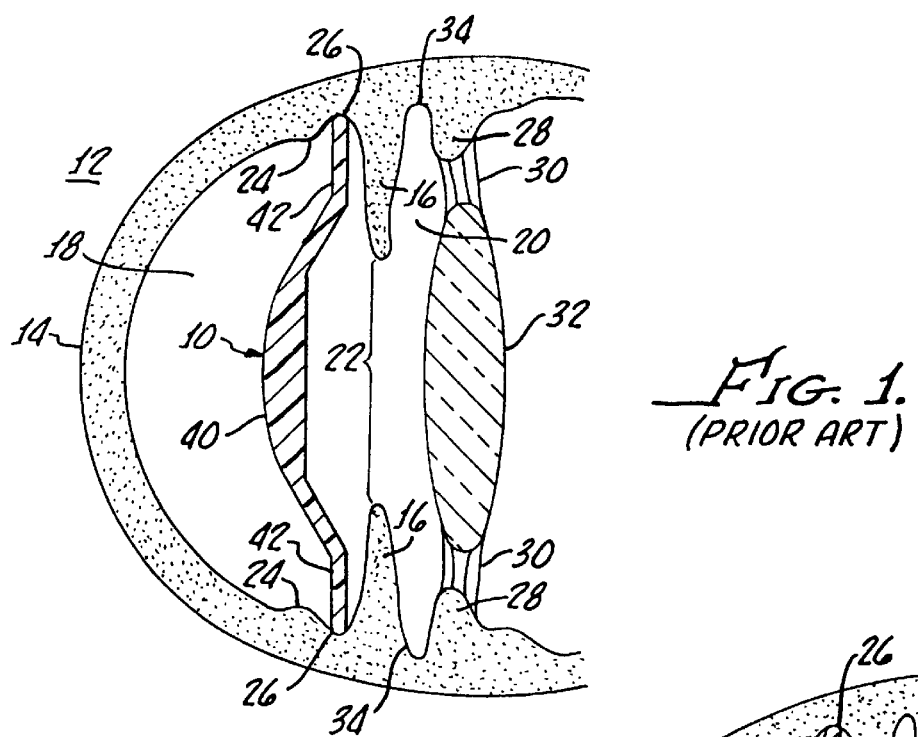
FIG. 1 is a vertical sectional view of an eye and an exemplary anterior intraocular lens of the prior art implanted therein.
Figure 2:
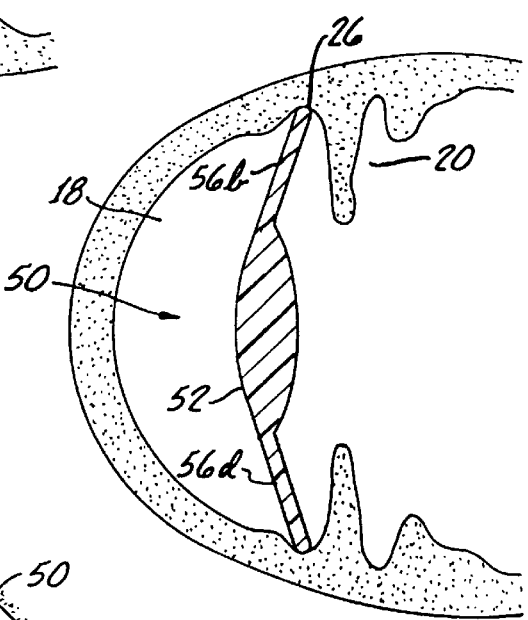
FIG. 2 is a vertical sectional view of an eye and an exemplary anterior intraocular lens of the present invention implanted therein.
Figure 3:
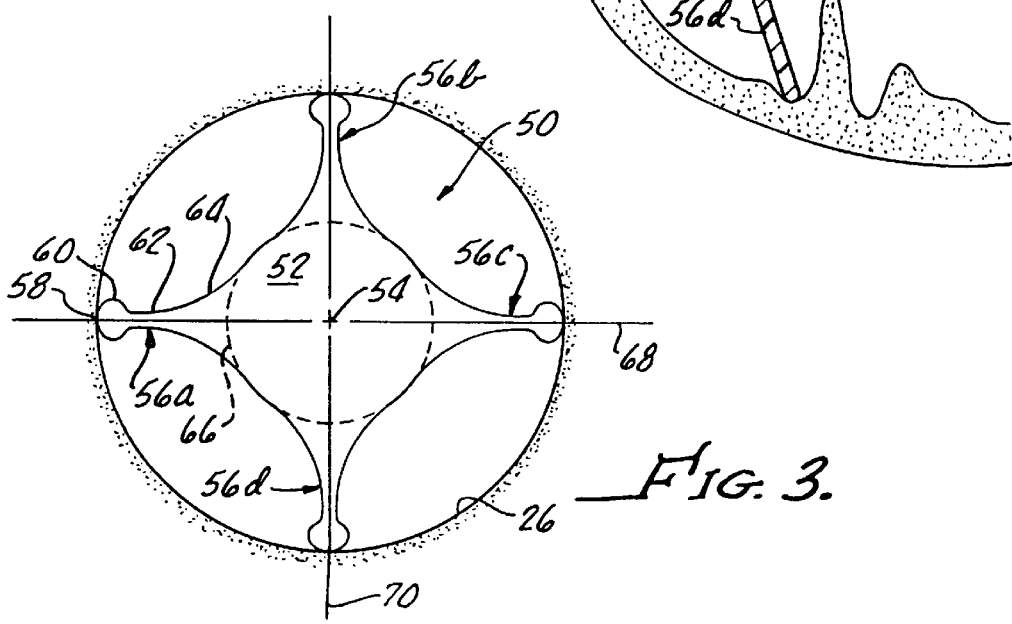
FIG. 3 is a front elevational view of a first embodiment of an intraocular lens of the present invention having four radially directed fixation members.

With reference to FIGS. 2 and 3, a first embodiment of an IOL in accordance with the present invention, shown generally at 50, is seen in elevational view mounted within a peripheral region of the anterior chamber 18. The IOL 50 comprises a central optic 52 having an optical axis 54, and a plurality of fixation members 56a–d. In this embodiment, there are four such fixation members 56 distributed equally about the circumference or periphery of optic 52. Each fixation member 56 is coupled or attached to the optic 52 and extends outwardly substantially the same distance therefrom into contact with the peripheral "angle" or ciliary band 26. The four distal ends 58 preferably are located in substantially the same plane. In this manner, the fixation members 56 support the optic 52 and maintain the optical axis 54 properly positioned within the anterior chamber 18.

The fixation members 56 may be constructed of a different material than optic 52, or alternatively may be formed integrally or unitarily as a single piece with the optic. Desirably, the optic 52 and fixation members 56 are polymeric and resiliently deformable. For example, the optic 52 and fixation members 56 may be formed from polymethylmethacrylate, silicone polymeric materials, acrylic polymeric materials, hydrogel-forming polymeric materials and mixtures thereof. The optic 52 and/or fixation members 56 may be substantially rigid. Desirably, the optic 52 is disk-shaped, preferably having a substantially lenticular cross-section, as seen in FIG. 2. Although the optic 52 preferably is substantially circular in a plane perpendicular to the optical axis 54, the optic may have any suitable configuration. Also, the optic 52 has an anterior face and a posterior face which may independently have any configuration, e.g., convex, concave, plano and the like, suitable to meet the vision needs of the patient wearing IOL 50. In addition, FIG. 2 illustrates the fixation members 56 extending in a posterior direction from the optic 52, and each may be planar or curvilinear.

In one embodiment, the IOL of the present invention is made of a material that is resilient enough to be folded for insertion through narrow or small incisions, for example, on the order of about 3.5 mm or smaller, in the sclera or cornea, into the anterior chamber of the eye. is more symmetric than that of the prior art, and is generally too wide to be inserted through small incisions without being first folded or otherwise deformed for insertion.

The four fixation members 56 of the IOL 50 seen in FIG. 3 are identical and extend directly radially outwardly from the optic 52. More specifically, each fixation member 56 terminates at a radially outward distal end 58 designed to safely contact the ciliary band or angle 26. The distal end 58 preferably includes an enlargement 60 relative to a proximal neck portion 62 that is located between the enlargement and the optic 52. In the embodiment shown in FIG. 3, the cross-section of each fixation member 56 narrows to a minimum at the neck portion 62. From the neck portion 62, each fixation member 56 gradually increases in a proximal direction through a shoulder portion 64 to smoothly join on both sides substantially along tangent lines of a circle 66, the circle generally defining the operating portion of the optic 52.

As mentioned, each of the four fixation members 56 extends directly radially outwardly from the optic 52 and is substantially evenly circumferentially distributed, along with the other fixation members, about the optical axis 54. Therefore, FIG. 3 illustrates two orthogonal axes 68 and 70 passing through the optical axis 54, and along which the four fixation members 56 extend. Because the fixation members 56 have the same radial dimension, imaginary lines drawn connecting the distal ends 58 define a square. As a result of the equidistant circumferential spacing, the IOL 50 exerts substantially uniform reaction forces against the ciliary band or angle 26 through the fixation members 56. More to the point, the optic 52 is positioned in the anterior chamber 18 by the fixation members 56 with a reduced risk of causing ovalling of the pupil.

The enlargement 60 can be a variety of shapes, as long as the edge contacting the ciliary band or angle 26 is rounded or otherwise shaped to reduce the risk of injury to the ciliary band 26 relative to a substantially identical IOL with fixation members including no such enlargements. For example, the enlargement 60 can be substantially disk-shaped, semi-circular, spherical, bulbous or other such shape. As will be apparent to one of skill in the art, the relatively large contact surface at the distal end 58 of each fixation member 56 helps to reduce contact stresses imparted to the ciliary band 26. This in turn reduces irritation of the ciliary band 26. In addition, the enlargement 60 on the distal ends 58 may be solid, but may also be rings or have other suitable non-solid configurations (not shown).

The neck portion 62 provides flexibility to the fixation members 56 in both the plane common to the axes 68 and 70, and in the Z-axis perpendicular to said plane. Because of the flexibility of the fixation members 56, the IOL 50 is able to respond to dynamic fluid forces within the anterior chamber 18, and to muscular movements of the ciliary band 26. At the same time, the gradually widening neck portion 62 reduces the stress level in each fixation member 56 adjacent the optic 52.

FIG. 4 illustrates an alternative IOL 80 in accordance with the present invention. Except as expressly described herein, IOL 80 is constructed and functions similarly to IOL 50.

IOL 80 includes a centrally located optic 82 supported by three fixation members 84a–c. As with the embodiment shown in FIG. 3, the optic 82 has an operating or optical portion generally defined within a circle indicated by the dashed line 86. The optic 82 has a central optical axis 88. In addition, the fixation members 84 are coupled or attached to the optic 82 and extend radially outward therefrom into contact with the ciliary band or angle 26.

Each of the fixation members 84a–c comprises a distal end 90 having an enlargement 92 relative to an adjacent neck portion 94. The neck portion 94 becomes gradually wider in a proximal direction and terminates in a shoulder portion 96 adjacent the optic 82. As before, each of the enlargements 92 can be a variety of shapes, but are desirably rounded or otherwise shaped to reduce the contact stress and attendant irritation imparted on the ciliary band 26.

FIG. 4 illustrates three rays 100a–c extending radially outward from the optical axis 88 and distributed 120 degrees with respect to each other. The distal end 90 of each of the fixation members 84 contacts the ciliary band 26 along one of the rays 100a–c. The fixation members 84 are thus distributed circumferentially evenly about the optical axis 88, and support the optic 82 within the anterior chamber 18 in a manner that reduces or even substantially eliminates the risk of ovalling the pupil. Stated another way, lines joining the three distal ends 90 define an equilateral triangle.

Rather than extending directly radially outward from the optic 82, the fixation members 84a–c extend outwardly in a spiral fashion (clockwise in accordance with the drawing). That is, the distal end 90 of each fixation member 84 lies along a radial line that is rotated with respect to a radial line passing through the associated shoulder portion 96. To illustrate, FIG. 4 shows a ray 102 passing approximately through the midpoint of the shoulder portion 96 of the fixation member 84a. The ray 100a passing through the distal end 90 of the same fixation member 84a is rotated in a clockwise direction by an angle 104 with respect to the ray 102.

Because the fixation members 84 extend in a spiral fashion from the optic 82, the wide shoulder portion 96 joins the optic on an outer side at an approximate tangent line with respect to the circle 86, and forms a tight curve on the inner side. This arrangement provides more radial flexibility for the fixation members 84 with respect to the fixation members 56 shown in FIG. 3. At the same time, the wide shoulder portion 96 helps to reduce stress adjacent the optic 82.

FIG. 5 illustrates a further IOL 110 in accordance with the present invention. Except as expressly described herein, IOL 110 is constructed and functions similarly to IOL 50.

IOL 110 has two pairs of connected fixation members. Again, the IOL 110 comprises a central optic 112 supported by a plurality of outer fixation members 114a–d, in this case four, in contact with the ciliary band or angle 26. The optic 112 is supported by the fixation members 114 in the anterior chamber.

Orthogonal axes 118 and 120 passing through the optical axis 116 are shown, and the distal ends 122 of the four fixation members 114 each lie at the intersection of one of these axes 118 and 120 and the ciliary band 26. Because of the size and configuration of the fixation members 114, lines connecting the distal ends 122 define a square. In other words, the distal ends 122 of the fixation members 114 are circumferentially distributed evenly about the optical axis 116 and serve to support the optic 112 while reducing the risk of ovalling of the pupil.

The IOL 110 defines something of an H-shape, with the optic 112 positioned along the bridge of the H. Each of the legs of the H defines two of the fixation members 114. That is, the fixation members 114a and 114b are generally co-linear and project in opposite directions, as are the fixation members 114c and 114d. Each pair of coupled fixation members 114 associated with each leg of the H is attached to the optic 112 at a common bridge portion 124 that is relatively narrow and widens at a shoulder portion 126 providing a smooth transition to the optic. Again, an imaginary circle 128 is shown to represent the boundary of the operating portion of the optic 112, and thus the boundary of the shoulder portion 126.

Each leg of the H-shaped IOL 110 comprises a central junction region 130 radially outward from the bridge portion 124. The two associated fixation members 114 project directly away from the junction region 130, and each other, generally along a chordal line of the ciliary band 26.

Each fixation member 114 terminates at the distal end 122 in an enlargement 132, which is wider than an adjacent primary neck 134. Continuing from the primary neck 134 away from the distal end 122, a reinforced portion 136 is provided, and then a secondary neck 138 joins to the junction region 130. In the illustrated embodiment, the IOL 110 is symmetric about both a vertical line, and about a horizontal line.

As was explained above, the narrowed bridge portion 124, and primary and secondary necks 134, 138 provides suitable flexibility for the IOL 110 to respond to dynamic forces within the eye. In addition, the shoulder portion 126, junction region 130, and reinforced portion 136 provide suitable structural strength to enable the fixation members 114 to center the optic 112, and reduce the level of stress at any one point. Finally, the relatively large radius of curvature of the enlargement 132 helps reduce irritation to the ciliary band 26.

FIG. 6 illustrates a still further embodiment of an IOL 140 in accordance with the present invention. Except as expressly described herein, IOL 140 is constructed and functions similarly to IOL 50.

The IOL 140 comprises an optic 142 centered about an optical axis 144, and a pair of members 146a–b.

Each member 146 extends outward from the optic 142 and contacts the ciliary band 26 at two points. More specifically, the upper and lower members 146a,b are shaped somewhat like a foot with a toe portion 150, a foot portion 152, a heel portion 154, and an ankle portion 156. The ankle portion 156 narrows to a bridge portion 158 that attaches or is coupled to the optic 142. The toe portions 150 of each member 146 point in a counter clockwise direction with respect to the optical axis 144. That is, each fixation member 146 first extends generally directly radially outward from the optic 142 along the bridge portion and ankle portion 156 to contact the ciliary band 26 at the heel portion 154. The foot portion 152 extends generally along a chordal line with respect to ciliary band 26 and terminates at the toe portion 150. Again, the optical zone of optic 142 is defined generally within a circle 160.

Both the toe portion 150 and heel portion 154 of the two members 146 contact the ciliary band 26 and are distributed circumferentially evenly about the optical axis 144. Therefore, while the IOL 140 is defined as having two members 146, the IOL 140 has four fixation members with each of the toe portions 150 and heel portions 154 considered the distal end of separate, connected fixation members. Consequently, then there are two pairs of connected fixation members, each connected pair being joined to the optic 142 at a common point.

Two orthogonal axes 162 and 164 are shown intersecting at the optical axis 144. Both toe portions 150 contact the ciliary band 26 along the first axis 162, while both heel portions 154 contact the ciliary band 26 along the second axis 164. In other words, imaginary lines drawn connecting the toe portions 150 and heel portions 154 define a square. Because of the particular shape of the IOL 140, half of the lens is a mirror image of the other half as viewed across either axis 162 or 164. As in the earlier embodiments, therefore, the IOL 140 prevents ovalling of the pupil.

As can be appreciated from the foregoing, the present IOL may have three, four, or even more fixation members circumferentially distributed in an even fashion about the optical axis. The fixation members may extend directly radially outward from the optic, or may be formed in a variety of shapes. More particularly, the fixation members may all be identically formed, or subsets of the fixation members may be identical with some being different. The IOL may be symmetric about one or more axes, or a portion may be formed as a mirror image of another portion.

While this invention has been described with respect to various specific examples and embodiments, it is to be understood that the invention is not limited thereto and that it can be variously practiced within the scope of the following claims.

What is claimed is:

1. An intraocular lens for implantation in an eye, the intraocular lens comprising:
   a resiliently deformable optic having an optical axis and being deformable to pass through a small incision into an eye; and
   at least three fixation members coupled to the optic and structured to be placed in an anterior chamber of a mammalian eye when the intraocular lens is in use, each of the fixation members having a distal end extending radially outwardly from the optic a distance from the optical axis, the distance being substantially the same for all of the fixation members, each of the distal ends being substantially equidistantly spaced apart from the closest circumferentially adjacent distal ends and including a structure enlarged relative to a portion of the elongated fixation member proximal of the distal end.

2. The intraocular lens of claim 1 which includes only three or only four fixation members.

3. The intraocular lens of claim 1 wherein each of the fixation members is substantially identically structured.

4. The intraocular lens of claim 1 wherein all of the distal ends of the elongated fixation members are located in substantially a single plane.

5. The intraocular lens of claim 1 which includes four fixation members and each of the distal ends is located at substantially a different corner of a single square.

6. The intraocular lens of claim 1 which includes three fixation members and each of the distal ends is located at substantially a different corner of a single equilateral triangle.

7. The intraocular lens of claim 1 which is sized and adapted to be placed in the mammalian eye so that the distal ends are located in contact with a peripheral region of the anterior chamber.

8. The intraocular lens of claim 1 wherein the optic is substantially circular in a plane perpendicular to the optical axis.

9. The intraocular lens of claim 1 which is a single piece lens.

10. The intraocular lens of claim 1 wherein the optic and the fixation members comprise one or more polymeric materials.

11. The intraocular lens of claim 1 wherein the optic comprises a material selected from the group consisting of silicone polymeric materials, acrylic polymeric materials, hydrogel-forming polymeric materials and mixtures thereof.

12. An intraocular lens for implantation in an eye, the intraocular lens comprising:
    a resiliently deformable optic having an optical axis and being deformable to pass through a small incision into an eye;
    a fixation system coupled to the optic and including at least three distal ends extending radially outwardly of the optic and structured to be in contact with a peripheral region of an anterior chamber of the eye;
    each of the distal ends being substantially equidistantly spaced apart from the closest circumferentially adjacent distal ends, and including a structure enlarged relative to a portion of the fixation system proximal of the distal end; and
    wherein, with the intraocular lens fixated in an anterior chamber of an eye having an iris, the intraocular lens is structured and sized to be effective to reduce malshaping of the iris relative to a substantially identical intraocular lens including distal ends each of which is not substantially equidistantly spaced apart from the closest circumferentially adjacent distal ends.

13. The intraocular lens of claim 12 wherein each of the distal ends is equidistantly spaced apart from the optical axis.

14. The intraocular lens of claim 12 which includes only three distal ends or only four distal ends.

15. The intraocular lens of claim 12 wherein all of the distal ends are located in substantially the same plane.

16. The intraocular lens of claim 12 wherein each of the distal ends is located at substantially a different corner of a single square.

17. The intraocular lens of claim 12 wherein each of the distal ends is located in a substantially different corner of a single equilateral triangle.

18. The intraocular lens of claim 12 wherein the optic is substantially circular in a plane perpendicular to the optical axis.

19. The intraocular lens of claim 12 which is a single piece lens.

20. The intraocular lens of claim 12 wherein the optic and the fixation system comprise one or more polymeric materials.

21. The intraocular lens of claim 12 wherein the optic comprises a material selected from the group consisting of silicone polymeric materials, acrylic polymeric materials, hydrogel-forming polymeric materials and mixtures thereof.

22. The intraocular lens of claim 12 wherein each of the structures are solid.

* * * * *

UNITED STATES PATENT AND TRADEMARK OFFICE
CERTIFICATE OF CORRECTION

PATENT NO.   : 6,475,240 B1
DATED        : November 5, 2002
INVENTOR(S)  : Paul

It is certified that error appears in the above-identified patent and that said Letters Patent is hereby corrected as shown below:

<u>Title page,</u>
Item [74], *Attorney, Agent, or Firm,* "Peter Jay Gluck" should read
-- Peter Jon Gluck --.

<u>Column 4,</u>
Line 2, "is more symmetric than" should read -- The configuration of the fixation members disclosed herein is more symmetric than --.

Signed and Sealed this

Third Day of June, 2003

JAMES E. ROGAN
*Director of the United States Patent and Trademark Office*